United States Patent [19]

Ofer et al.

[11] Patent Number: 5,627,472
[45] Date of Patent: May 6, 1997

[54] CONDITION TESTER FOR A BATTERY

[75] Inventors: David Ofer, Newton, Mass.; Gary M. Searle, North Smithfield, R.I.; Joseph Bernier, Cambridge, Mass.

[73] Assignee: Duracell Inc., Bethel, Conn.

[21] Appl. No.: 378,688

[22] Filed: Jan. 26, 1995

[51] Int. Cl.$^6$ .......................... G01N 27/416; G01R 31/36
[52] U.S. Cl. ........................ 324/435; 320/48; 429/92
[58] Field of Search .................................. 324/426, 427, 324/435; 340/636; 320/48; 429/90, 91, 92, 93

[56] References Cited

U.S. PATENT DOCUMENTS

| | | | |
|---|---|---|---|
| 3,045,178 | 7/1962 | Corrsin | 368/114 |
| 3,343,083 | 9/1967 | Beusman | 324/94 |
| 3,431,481 | 3/1969 | Smyth | 320/48 |
| 4,723,656 | 2/1988 | Kiernan et al. | 206/705 |
| 5,250,905 | 10/1993 | Kuo et al. | 324/435 |
| 5,339,024 | 8/1994 | Kuo et al. | 324/435 |
| 5,355,089 | 10/1994 | Treger | 324/435 |
| 5,396,177 | 3/1995 | Kuo et al. | 324/435 |
| 5,411,817 | 5/1995 | Ridgway et al. | 429/90 |
| 5,418,086 | 5/1995 | Bailey | 429/93 |
| 5,537,390 | 7/1996 | Horiba et al. | 320/48 X |

*Primary Examiner*—Kenneth A. Wieder
*Assistant Examiner*—Glenn W. Brown
*Attorney, Agent, or Firm*—Robert J. Feltovic; Rose M. Allen; Barry D. Josephs

[57] ABSTRACT

A tester for determining the condition of an electrochemical power source, e.g. a battery or main cell, is disclosed. The tester may comprise an electrolytic (coulometric) cell connected in series to a auxiliary cell. The auxiliary cell is a miniature electrochemical power cell. The electrolytic (coulometric) cell may have no electromotive force of its own and may comprise an anode and cathode of the same material, desirably silver, with an electrolyte contacting at least a portion of both the anode and cathode. The tester may be permanently connected in parallel to a main cell being tested and is thin enough to be integratable into a label for the main cell. As the main cell discharges, the electrolytic cell anode clears proportionally to the discharge of one of the electrodes of the main cell to provide a continuous visually discernible indication of the state of charge of the main cell.

13 Claims, 6 Drawing Sheets

CONDITION TESTER FOR A BATTERY

This invention relates to a condition tester for determining the condition of a battery or main cell and integrally relating the tester thereto. The invention relates to state of charge (coulometric) testers.

Electrical primary cells which include devices for visually indicating the condition or state of charge of the cell are known. The known indication devices include, but are not limited to, chemical indicators which react with materials inside the battery, chemical indicators located externally to the battery, elements embedded within an electrode that become visible during discharge, and thermochromic materials in thermal contact with a resistive element that is adapted to be connected across the battery. A problem with many of these indicators is the timing of their indication is sensitive to the construction geometry of the indicator on or within the battery. Therefore, natural variations which inherently occur during manufacture lead to variability, from battery to battery, in the time during discharge when the indication occurs.

Commercially available testers to determine the condition of an electrochemical cell are typically of the thin film heat responsive type. This type of tester contains a thermochromic material in thermal contact with an electrically conductive element. Such testers are commercially available in the form of strips which are not integrated into the cell or cell label. To use the tester one must apply it to the terminal ends of the cell being tested. Examples of such testers and their application are disclosed in U.S. Pat. Nos. 4,723,656 and 5,188,231. These testers work well for intermittent testing of a battery during its useful life. They are more difficult to permanently attach to a battery because the visual indicator is a thermochromic material. Care must be taken to thermally insulate the indicator from the battery casing in order to prevent heat transfer that would interfere with proper operation of the indicator. Additionally, the electrically conductive element is connected in series with, and drains the battery during the test. Therefore, the electrical contacts of the tester cannot be permanently attached to the battery terminals in the absence of an activatable contacting device, otherwise, the battery would be prematurely discharged through the tester.

Another type of battery tester is an electrochemical tester which has an electromotive force (e.m.f.) of its own as disclosed in U.S. Pat. No. 5,250,905. Such tester has the advantage that it may be permanently attached to the battery being tested and does not require activatable contacting devices. This type of tester provides visual indication of the battery's extent of discharge by the extent to which a thin film of metal is electrochemically stripped or cleared to reveal a background of different color.

Coulometric devices can keep track of the coulombs of electrical charge that pass through electronic equipment with which they may be associated. Examples of coulometric devices which use the electrochemically induced change in length of a column of mercury to give visual indication of the quantity of charge passed are disclosed in U.S. Pat. Nos. 3,045,178 and 3,343,083. Coulometric devices do not have an electromotive force of their own and have not been successfully applied to primary batteries.

The present invention discloses a thin film electrolytic cell which functions as a coulometer and gives a continual visual indication of state of charge of a main cell or battery being tested.

The invention will be better understood with reference to the drawings in which.

The invention is directed to a condition indicator (tester) which is electrically connected to and visually displays the condition of an electrochemical power source, e.g., a battery. The condition indicator comprises a coulometric cell which is an electrolytic cell comprising an anode, a cathode, and an electrolyte contacting at least a portion of both said anode and cathode. The electrolytic cell has essentially no electromotive force (e.m.f.) of its own and its anode and cathode are desirably of the same material, preferably silver. The condition indicator is thin and may be integrated into the label for a battery being tested. In a principal aspect the condition indicator further comprises an auxiliary cell electrically connected in series to the electrolytic cell. The auxiliary cell is a power generating cell other than the power source being tested and is electrically connected either positive to positive or negative to negative with the power source, e.g. battery, being tested. This produces a low net voltage available to drive the electrolytic cell. As the electrochemical power source discharges, the auxiliary cell discharges in a proportional amount. Electrolysis occurs in the electrolytic cell coulombically equal to the coulombic discharge of the auxiliary cell. Thus, the electrolytic cell also discharges proportionally to the main cell. During electrolysis at least one of the anode and cathode of the electrolytic cell is visible and a change occurs in the visible electrode. The amount of change, e.g. depletion, in the visible electrode, normally the anode, provides a visual indication of the state of charge (the percent remaining capacity) of the electrochemical power source being tested.

In other aspects, the invention is directed to the electrolytic cell portion of the condition indicator connected across a shunt resistor located either on the anode or cathode side of a battery being tested. In such cases the auxiliary cell may be eliminated, although its inclusion is nonetheless preferred to increase control over the operation of the electrolytic cell.

Figure 2:
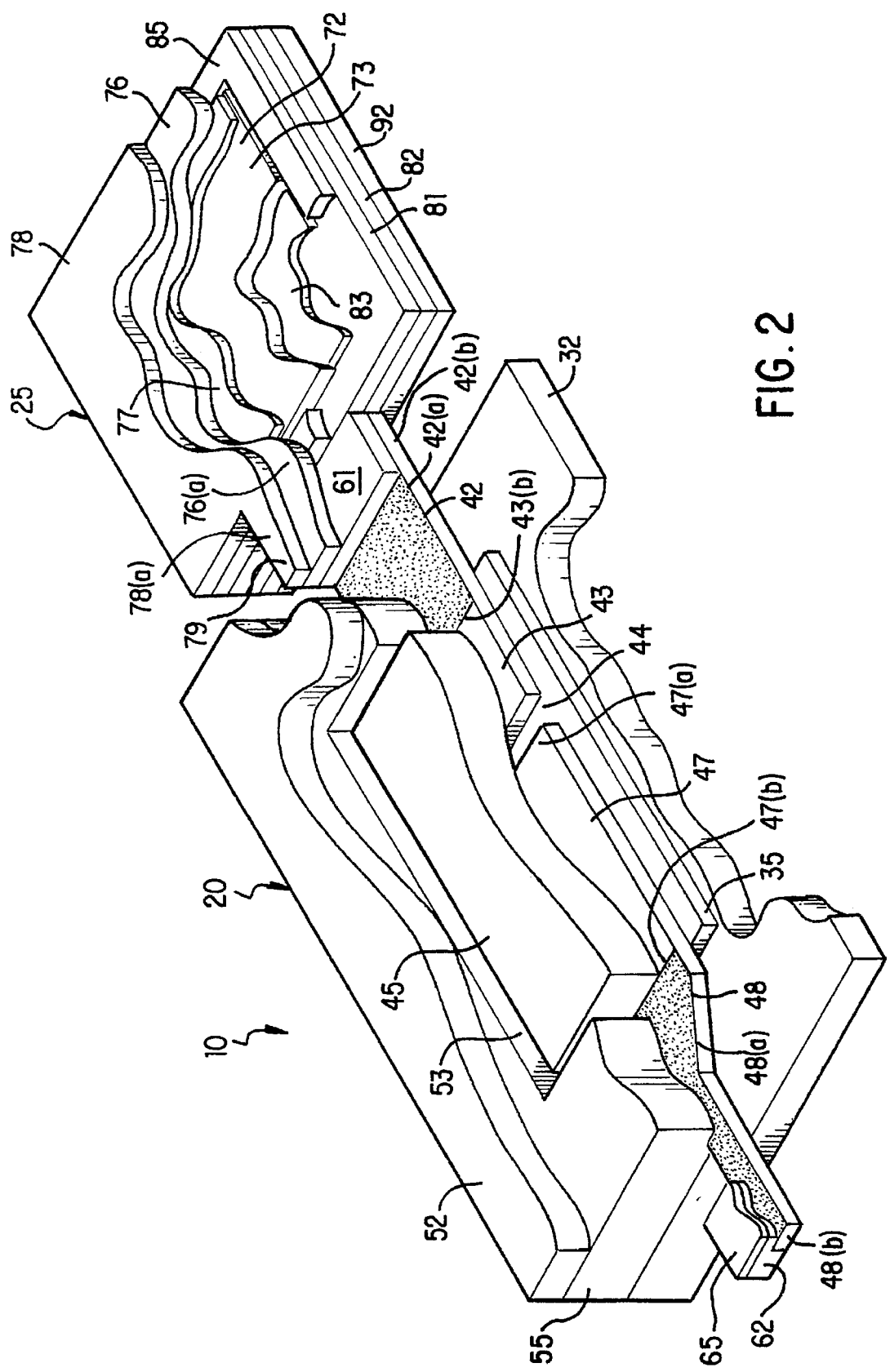
FIG. 2 is a cutaway perspective view of the tester assembly referenced in FIG. 1.

In a specific embodiment (FIG. 2) the tester 10 (condition indicator) of the invention comprises a coulometric cell 20 connected in series with an auxiliary cell 25. Tester 10 as a whole can be connected in parallel to the main cell 30 being tested. Coulometric cell 20, illustrated best in FIG. 2, is a miniature electrolytic cell having essentially no electromotive force (e.m.f.) of its own, that is, less than about 100 millivolts and preferably zero volts. Electrolysis resulting in depletion of one of the electrodes in coulometric cell 20 occurs when current passes through it. The auxiliary cell 25 is a miniature electrochemical cell which helps to control the operation of coulometric cell 20. Tester 10 can be connected in parallel to the main cell 30 being tested. Preferably, auxiliary cell 25 is connected to the main cell so that either the anode 77 of the auxiliary cell is electrically connected to the anode 115 of the main cell or the cathode 83 of the auxiliary cell is electrically connected to the cathode 145 of the main cell. Such connection results in a very low net voltage available to drive the coulometric cell during load discharge of the main cell. Also the coulometer cell 20 is connected to main cell 30 so that either the anode of the coulometer cell is electrically connected to the positive terminal of the main cell or the cathode of the coulometer cell is electrically connected to the negative terminal of the main cell. Additionally, the open cell voltage (OCV) of the auxiliary cell 25 is substantially similar, e.g. within about 100 millivolts, to the open cell voltage of main cell 30. This prevents discharge of coulometer cell 20 before load 38 is connected to main cell 30. In the preferred embodiment voltage across the coulometer cell 20 is very low so that it does not noticeably alter the voltage-capacity profile of the auxiliary cell. The electrochemistry of the auxiliary cell 25 and thus the voltage-capacity profile of the auxiliary cell is preferably similar to that of the main cell. This ensures that the auxiliary cell 25 discharges linearly proportionally to that of the main cell 30. The coulometer cell which is in series with the auxiliary cell discharges linearly proportionally to the auxiliary cell 25 and thus also main cell 30.

Figure 1:
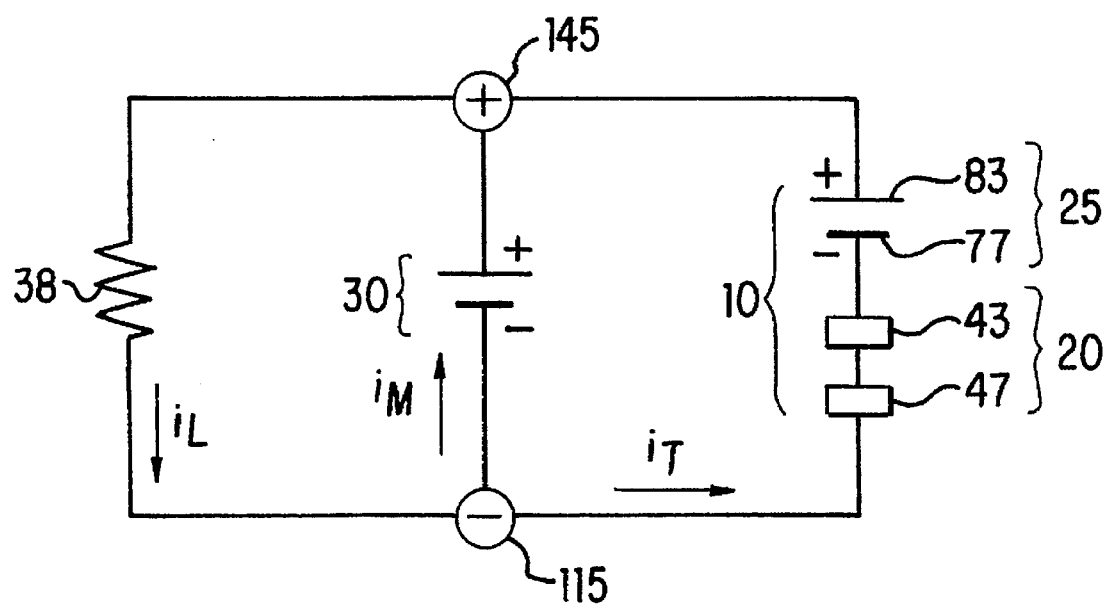
FIG. 1 is a circuit diagram showing the connection of the tester assembly of the invention to the main cell being tested.

In the preferred circuit arrangement, depicted in FIG. 1, the auxiliary cell anode 77 is electrically connected to the coulometric cell cathode 43, the auxiliary cell cathode 83 is connected to the main cell cathode 145, and the coulometric cell anode 47 is connected to the main cell anode 115. (The anode of either the auxiliary cell 25 or coulometric cell 20 is defined as the electrode being oxidized and thus releasing electrons.)

Tester 10 comprising a coulometric cell 20 and auxiliary cell 25 is shown in FIG. 2 in an arrangement consistent with the circuit diagram of FIG. 1. Tester 10 may be permanently connected to a main cell 30 (FIG. 2A), such as a conventional alkaline cell, for example, by integrating it into the label for the main cell. The voltage of the tester follows that of the main cell because the tester's capacity is much lower and its resistance is much higher. Therefore, for electrochemically equivalent main cell-auxiliary cell combinations having identical capacity/voltage characteristics, as the main cell discharges the ratio of current flow through the main cell to the current flow through the auxiliary cell stays at nearly constant value. This will be so irrespective of the load on the main cell. Thus, at any time during discharge of the main cell, the percent depletion of one of the anode or cathode of the auxiliary cell will be about the same as the percent depletion of one of the anode or cathode of the main cell. (If the amount of anode active material or cathode active material in either the main cell or auxiliary cell is in excess, the comparison of percent depletion between the two cells should be made using the electrode containing active material not in excess. The electrode not in excess may be referred to herein as the controlling electrode.)

If tester 10 is constructed so that the charge capacity of the coulometer anode 47 is equal to that of the auxiliary cell controlling electrode, then at any time during discharge of the auxiliary cell the percent depletion of the anode of the coulometric cell 20 will be controlled by and be about the same as the percent depletion of the controlling electrode of the auxiliary cell. Thus, the percent depletion (clearing) of the anode of coulometric cell 20 reflects the percent depletion of a controlling electrode in the main cell. This can be used to provide a continual visual indication of the condition (state of charge) of the main cell. The percent active material remaining in the coulometric cell may be visually discernible at any time during the life of the main cell. For example, if the coulometric anode is being depleted, the anode may be made visually discernible and a graphics scale positioned next to that anode may indicate the percent charge remaining in the main cell and/or whether the main cell needs to be replaced. During electrolysis as anode material depletes it characteristically plates onto the cathode resulting in enlargement of the cathode. In such case the cathode may be made visually discernible and a graphics scale placed next to it to indicate percent charge remaining in the main cell.

Tester 10 may be connected in parallel with main cell 30 being tested, for example, as illustrated in the circuit diagram of FIG. 1. In FIG. 1 the main cell 30 is shown schematically with negative terminal 115 and positive terminal 145. In use, when main cell 30 is connected to a load 38 and discharges, current $i_L$ flows through the load 38, current $i_M$ flows through the main cell and current $i_T$ flows through tester 10 such that $i_L = i_M + i_T$. The resistance of auxiliary cell 25 is desirably much higher than the internal resistance of main cell 30, and the resistance of coulometer cell 20 in turn is much higher than the resistance of auxiliary cell 25. For example, in the circuit configuration of FIG. 1, if the main cell is a conventional AA size alkaline cell having an internal resistance of about 0.1 ohm during normal operation, the resistance of auxiliary cell 25 may desirably be between about 500 and 2000 ohms and the resistance of coulometer cell 20 may desirably be between about 4000 and 8000 ohms. The auxiliary cell voltage will be slightly higher than the main cell voltage for any given load on the main cell. This small difference in voltage results in a small net voltage available to drive the auxiliary cell 25 during load discharge of the main cell. For example, at a typical load between 70 ohm and 1 ohm for a conventional AA 1.5 volt main cell, the net voltage driving the auxiliary cell 25 is between 0.05 and 0.1 volt and the current flow through coulometer cell 20 may typically be between about $0.05 \times 10^{-6}$ amp and $5 \times 10^{-6}$ amp.

In the preferred embodiment of tester 10 (FIG. 2), auxiliary cell 25 is a miniature flat electrochemical power source which at least partially drives coulometric cell 20. Main cell 30 may be a primary or secondary battery and typically may be a conventional alkaline cell. Tester 10 is a flat assembly of thickness less than about 100 mils (2.5 mm), preferably between about 2 and 100 mils (0.05 and 2.5 mm), more preferably between about 2 and 15 mils (0.05 and 0.4 mm). Tester 10 may be integrated into the label for the main cell 30, for example, by attaching it to the inside surface of the label. Coulometric cell 20 contains an anode 47 and cathode 43 advantageously composed of the same material. The auxiliary cell 25 discharges linearly proportional to the dishcarge of discharge of the main cell 30, irrespective of load 38. For example, auxiliary cell 25 can be calibrated so that during discharge of main cell 30 the percentage discharge of either the anode or cathode of the auxiliary cell 25 will be the same as or at least a linear function of the percent discharge of a controlling electrode of main cell 30.

Coulometric cell 10 (FIG. 2) is a miniature electrolytic cell containing a cathode material 43 and anode material 47 which are desirably spaced apart from each other, and which may lie in the same plane. Coulometric cell 10 has a thickness less than 100 mils (2.5 mm), preferably a thickness between about 2 and 100 mils (0.05 and 2.5 mm), more preferably a thickness between about 2 and 15 mils (0.05 and 0.4 mm). Cathode 43 and anode 47 are desirably of the same metal which can be easily electrochemically plated and stripped (having relatively high current density at low driving voltage) when in contact with an electrolyte containing the ion of that metal. Cathode 43 and anode 47 are thin coatings deposited onto substrates 42 and 48, respectively. It is desirable that the metal used for cathode 42 and 48 not be reactive in the ambient atmosphere or subject to corrosion. As a practical measure, silver is preferred for cathode 43 and anode 47, because it has high electrochemical activity and is noble and unreactive with ambient oxygen and moisture. Anode substrate 48 is conductive and preferably of carbon and cathode substrate 42 is preferably also conductive and of carbon. (It is possible to use a nonconducting material for cathode substrate 42, but a conducting substrate is preferred and will be described herein.) A conducting anode substrate 48 is required in order that electrically isolated islands of metal not be left behind as anode 47 is electrochemically stripped (cleared) from one end to the other. A further requirement is that anode substrate 48 be of a color that provides high contrast to the color of anode 47, thus giving highly discernible visual indication of the clearing of anode 47. A preferred arrangement of cathode 43 and anode 47 in relationship to each other and the underlying conductive substrate is shown in FIG. 2. A space 44 separates cathode 43 from anode 47 and also separates underlying conductive substrates 42 from 48, as may be seen best in FIG. 2. Also, there may be a film of insulating material 35 under conductive substrates 42 and 48.

Figure 2A:
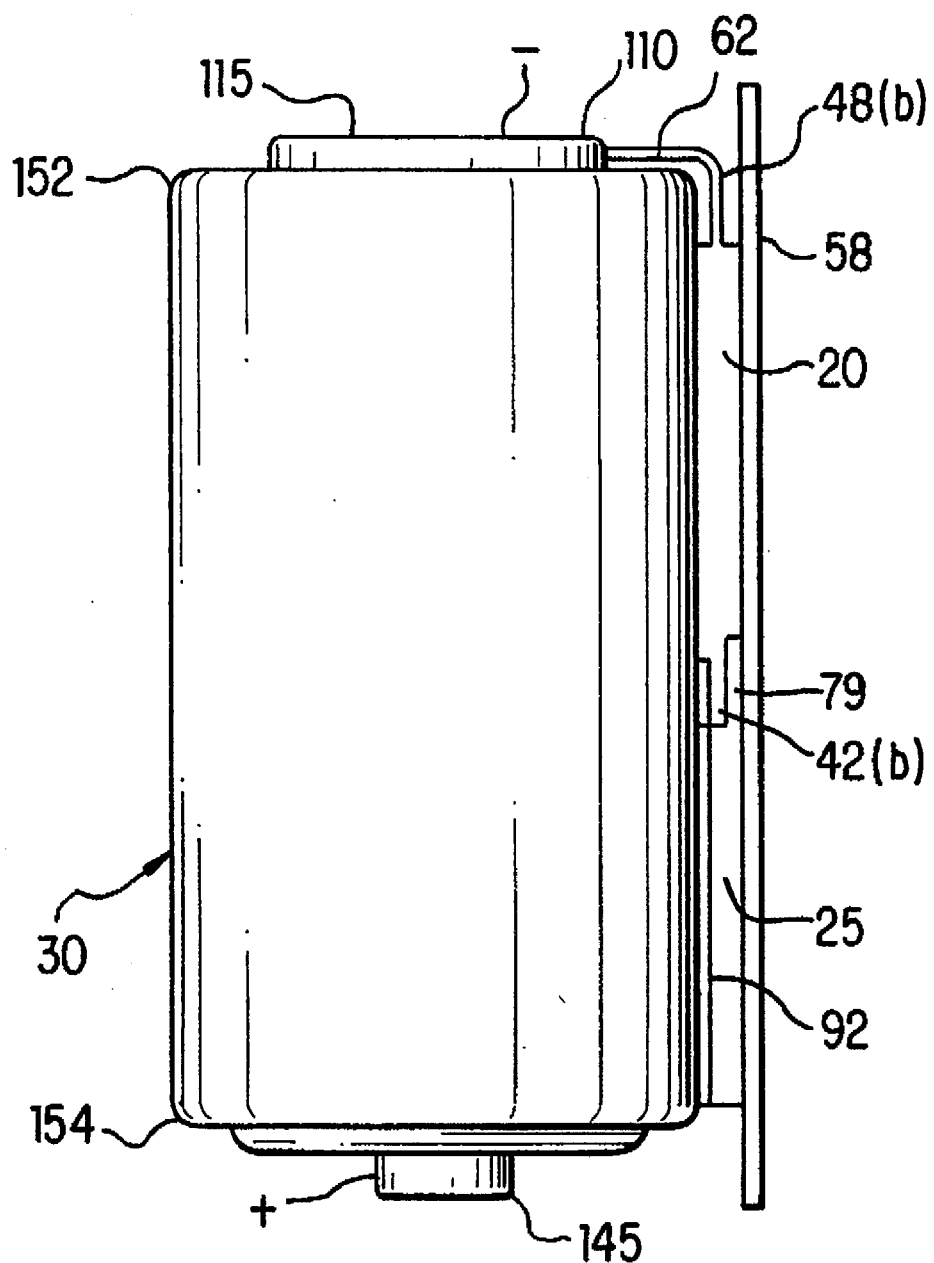
FIG. 2A shows a battery having a permanently connected tester with the tester in partial cross sectional view shown enlarged.

Conductive substrate 42 (FIG. 2) can extend beyond the edge 43(b) of the overlying cathode material to form extended substrate portions 42(a). Similarly conductive substrate 48 can extend beyond the edge 47(b) of the overlying anode material to form extended substrate portion 48(a). An adhesive is applied to the surface of extended portions 42(a) and 48(a), thus forming an adhesive border 55 around the periphery of conductive substrates 42 and 48. If cathode substrate 42 is not conducting, then cathode edge 43(b) must extend and continue outside adhesive border 55 in order to serve as the electrical contact at end 42(b). Adhesive border 55 defines a window space 53 over cathode 43 and anode 47. A layer of clear electrolyte 45 is applied in window space 53 so that it covers cathode 43 and anode 47. The end 48(b) of extended substrate portion 48(a) protrudes from the anode side of cell 20. Similarly the end 42(b) of extended substrate portion 42(a) protrudes from the cathode side of cell 20. A piece of aluminum foil 65 is attached to end portion 48(b) using conductive adhesive 62 placed therebetween. Foil 65 serves to carry current from substrate 48 to the battery negative terminal 115 (FIG. 2A). End portion 42(b) is covered on its top surface with conductive adhesive 61. A transparent barrier film 52 is applied over window 53 with the edges of the film in contact with adhesive border 55. Thus, barrier film 52 is a protective film which covers and tightly seals off electrolyte 45. Barrier film 52 is held in place by adhesive border 55. Coulometric cell 20 may be secured to the casing of main cell 30 with a pressure sensitive adhesive 32 applied the underside of the tester under insulating film 35.

Auxiliary cell 25 (FIG. 2) is desirably a flat power cell designed to have a similar open cell voltage as main cell 30. Additionally, it is desirable that auxiliary cell 25 exhibit capacity/voltage characteristics (open circuit voltage vs. percent capacity profile) similar to that of main cell 30. Auxiliary cell 25 has a thickness less than 100 mils (2.5 mm), preferably a thickness between about 2 and 100 mils (0.05 and 2.5 mm), more preferably a thickness between about 2 and 15 mils (0.05 and 0.4 mm). Auxiliary cell 25 contains a coating of anode active material 77, a coating of cathode active material 83, and electrolyte layer 73 therebetween. Cathode material 83 is preferably a coating of manganese dioxide applied to a conductive substrate containing a carbon filled plastic film 81. Cathode active material 83 is preferably manganese dioxide because it is the same cathode active material employed in main alkaline cell 30. This helps to ensure that auxiliary cell 25 and main cell 30 have similar capacity/voltage characteristics. The quantity of active material in cathode 83 must be such that it has the same coulombic capacity as coulometer anode 47. The opposite side of carbon filled film 81 is covered with conductive aluminum foil 82. Aluminum foil 82 serves as a vapor barrier to seal the auxiliary cell 25 from the environment and also may serve as a current collector for cathode 83. Carbon filled film 81 protects foil 82 from corrosion by electrolyte 73 while at the same time electrically contacting cathode 83 to foil 82. An insulating film 85 is applied around the border of the exposed edges of cathode layer 83. A separator 72 saturated with electrolyte 73 is applied over cathode active layer 83 within the space bounded by insulating border 85. Anode active material 77 contacts separator 72. Anode active material 77 may be a coating of zinc applied under a conductive substrate of carbon filled plastic film 76. The amount of anode active material 77 is preferably such that its coulombic capacity is considerably in excess of that of cathode 83. The opposite side of carbon filled film 76 is covered with a layer of conductive aluminum foil 78. A portion of foil 78 is left uncoated with anode active material. This portion forms the anode tab 79 which protrudes from the auxiliary cell. Anode tab 79 is composed of a protruding portion 78(a) of aluminum foil 78 and a protruding portion 76(a) of the underlying conductive layer 76. Anode active material 77 contacts electrolyte filled separator 72. A conductive adhesive 92 is applied to the underside of cell 25 in contact with the exposed surface of foil 82. Auxiliary cell 25 is secured to the main cell 30 through conductive adhesive 92 which secures cell 30 to the main cell housing.

The coulometric cell 20 (FIG. 2) is electrically connected to auxiliary cell 25 by applying the anode tab 79 so that the underlying conductive layer 76(a) of the anode tab contacts conductive adhesive 61 on tab 42(b). This electrically connects auxiliary anode active material 77 with cathode 43 of coulometric cell 20 consistent with the circuit diagram of FIG. 1. Connections to main cell 30, typically a conventional alkaline cell, is illustrated with reference to FIGS. 2 and 2A. Auxiliary cathode active material 83 becomes electrically connected to the positive terminal 145 of main cell 30 through conductive adhesive 92 (FIG. 2) which connects auxiliary cathode 83 to the main cell housing as shown in FIG. 2A. Foil tab 65 is pressed into permanent contact with negative end cap 110 of the main cell (FIG. 2A) so that conductive adhesive 62 contacts end cap 110. Such connection places anode 47 of coulometric cell 20 in electrical contact with the negative terminal 115 of the main cell 30.

Tester 10 may be integrated onto the inside surface of a film label 58 for the main cell as illustrated in FIG. 2A. Label 58 may desirably be a heat shrinkable film such as polyvinylchloride or polypropylene. Tester 10 may be formed on one side of the label by sequential printing or lamination of each of the coatings that comprise the coulometric cell 20 and auxiliary cell 25. A layer of heat resistant pressure sensitive adhesive, may be applied to the inside surface of the label and the label with integrated tester may be applied to main cell 30 by wrapping it around the cell housing. The ends of the label may then be heat shrunk over the top and bottom shoulders 152 and 154, respectively, in conventional manner by subjecting the edges of the label to sufficient heat to cause shrinkage.

In operation, whenever the main cell 30 discharges, auxiliary cell 25 discharges which in turn causes coulometric cell 20 to function. Specifically, in the embodiment shown in FIGS. 1 and 2 as the main cell 30 discharges, coulometric anode active material 47 becomes plated onto cathode 43. In the plating process anode active material 47 disappears gradually from the portion of anode active layer closest to cathode layer 43, namely, from end 47($a$) (FIG. 2). This provides a visually discernible fuel gauge effect. The amount of coulometric anode remaining in cell 20 at any time during the life of main cell 30 is readily visible through transparent electrolyte 45. A graphics scale may be placed adjacent coulometric anode 47. A graphics scale can be calibrated to indicate the degree to which coulometric anode 47 has been depleted and consequently whether main cell 30 needs to be replaced.

Tester 10 comprising coulometric cell 20 and auxiliary cell 25 has a high resistance so that the current passing therethrough on discharge is very small. Tester 10 exhibits essentially the same voltage vs. percent capacity profile as the main cell. The ratio of current, $i_T$ (passing through tester 10) to current $i_M$ (passing through main cell 30) is approximately the same irrespective of the resistance load on the main cell. Thus, for any given load on the main cell, the auxiliary cathode 83 discharges to approximately the same extent as the main cell cathode and in turn causes the coulometric anode 47 to clear to that same extent. Consequently, at any time during the life of the main cell the percentage discharge of the main cell cathode will be approximately the same as the percentage discharge of the auxiliary cathode 83 which in turn will be approximately the same as the percentage of coulometric anode 47 that has cleared. This enables easy determination of the degree of discharge of the main cell by visual inspection through window 53 of the amount of anode 47 remaining in coulometric cell 20. A calibrated graphics scale which may be provided adjacent coulometric anode 47 makes it easier to determine when anode 47 has been sufficiently depleted indicating that main cell 30 must be replaced.

The following materials can be used to construct tester 10: Coulometer cell anode substrate 48 may be composed of an insulating plastic such as KAPTON polyimide insulating film (E.I. Dupont Co.) coated with conducting carbon composition 48($a$). A suitable carbon coating 48(a) is a carbon-filled epoxy ink available under the trade designation 113–26 ink from Creative Materials Inc (CMI). Alternatively, anode substrate 48 may be composed of an insulating plastic film such as ACLAR film (polychlorotrifluoroethylene) from Allied Signal Co. or KALODEX film (polyethylene naphthalate) from ICI Americas coated with an electronically conducting film such as indium tin oxide (ITO) or conductive carbon coating. Alternatively, anode substrate 48 may formed of a conductive carbon-filled plastic such as carbon-filled fluorocarbon polymeric film available as X17611 carbon-filled film from W.L. Gore Co. Anode substrate 48 has a thickness desirably between about 0.5 and 1 mil. The coulometer cell anode 47 may be composed of a silver coating (thickness between 500 and 1000 angstrom) deposited on top of anode substrate 48 by sputtering or by electron beam evaporation.

The coulometer cell cathode substrate 42 may be formed of the same material and of same thickness as the above described anode substrate 48, or alternatively it may simply be an insulating plastic film such as ACLAR or KALODEX film. The coulometer cell cathode layer 43 may be composed of a silver coating (thickness between 500 and 1000 angstrom) deposited on top of cathode substrate 42 by sputtering or by electron beam evaporation.

The coulometer electrolyte 45 (FIG. 2) may be prepared by first forming an electrolyte solution of a coating composed of a mixture of silver trifluoromethanesulfonylimide (AgTFSI) in a 1:1 volume mixture of ethylene carbonate and 3-methylsulfolane solvent and then gelling the solution with poly(vinylidene fluoride). Electrolyte 45 may be prepared by mixing 8 parts by weight of the electrolyte solution with 3 parts by weight of poly(vinylidene fluoride). The mixture is extruded at a temperature of about 140° C. to the desired thickness, preferably between about 1 and 4 mils (0.025 mm and 0.10 mm) and applied over coulometer anode 47 and cathode 43.

The coulometer adhesive frame 55 (FIG. 2) may be selected from a wide range of pressure sensitive adhesives. A desirable adhesive is a conventional butyl rubber based adhesive such as polyisobutylene/isoprene copolymer adhesive available as Butyl 065 rubber adhesive from EXXON Co. Adhesive frame 55 desirably has a thickness between about 1 and 2.5 mil (0.025 mm and 0.0625 mm). Coulometer transparent barrier 52 may be desirably composed of ACLAR (polychlorotrifluoroethylene) film (Allied Signal Co.) of thickness between about 0.6 and 1 mil (0.015 and 0.025 mm). Conductive adhesive 62 may desirably be a carbon filled conductive adhesive such as that available under the trade designation ARCLAD conductive transfer adhesive from Adhesives Research Co. Adhesive coating 62 may desirably be about 0.5 mil (0.012 mm) thick. Foil backing 65 may desirably be of aluminum foil between about 0.25 and 0.5 mil (0.006 and 0.012 mm) thick.

The auxiliary cell cathode conductive substrate 81 may be composed of conductive carbon-filled poly(vinylacetate) /poly(vinyl chloride) polymer film (Rexham Graphics conductive plastic film no. 2664-01). As above described conductive layer 81 is laminated to a layer 82 of aluminum foil. The conductive polymer film may desirably be about 1 mil (0.025 mm) thick and the aluminum foil between about 0.25 and 0.5 mil (0.006 and 0.012 mm) thick. The auxiliary cell cathode 83 is desirably composed of a printed coating containing X% electrolytic manganese dioxide (EMD), (90–X)% graphite, and 10% polyvinylchloride binder. Cathode active layer 83 may be prepared by dispersing 3 parts by weight of the a mixture of EMD and graphite in 7 parts by weight of aqueous 0.75% Carbopol 940 (B.F. Goodrich Co.) crosslinked acrylic acid copolymer and adjusting the mixture to a pH of 10 with KOH and then adding HALOFLEX 320 (ICI Americas—U.S. Resins Division) PVC latex in sufficient amount that it comprises 10 wt. % of the final dried cathode material. The mixture is then coated as a wet film (0.2 to 0.5 mil thick) onto carbon-filled polymer layer 81 and then air dried to form dried cathode active layer 83. Auxiliary cell separator 72 may be a nitrocellulose or cellophane porous membrane of thickness about 1 mil (0.025 mm) containing about 2–8 microliters of an electrolyte solution 73 composed of about of 24 to 32% by weight aqueous ZnCl adjusted to a pH of 4 by adding ZnO.

The auxiliary cell anode substrate 76 may be composed of conductive carbon-filled poly(vinyl acetate)/poly(vinyl chloride) polymer film (Rexham Graphics conductive plastic film no. 2664-01). Substrate 76 is laminated to a layer 78 of aluminum foil. The conductive polymer film may desirably be about 1 mil (0.025 mm) thick and the aluminum foil between about 0.25 and 0.5 mil (0.006 and 0.012 mm) thick. The auxiliary cell anode layer 77 may be a coating composed of 90% zinc powder and 10% styrene-butadiene copolymer (SBR) binder. Anode layer 77 may be prepared by first dispersing 6.5 parts by weight Zn powder (5 to 7 micrometer particle size) in 3.5 parts by weight aqueous 1.25% Carbopol 940 crosslinked acrylic acid copolymer gel (adjusted to a pH of 12 with KOH). Then a styrene-butadiene rubber latex (ROVENE 5550 SBR latex from Rohm & Haas Co.) is added in amount sufficient to yield 1 part by weight styrene-butadiene rubber per 9 parts zinc in the final dry film. The mixture is then coated as a wet film (0.5 to 1.5 mil thick) onto carbon-filled polymer layer 76 and then air dried.

Auxiliary cell contact adhesive 61 and 92 may be selected from a variety of conductive adhesives. A suitable adhesive 61 or 92 may be a conductive carbon-filled transfer adhesive available as ARCLAD adhesive from Adhesives Research Co. Such adhesive may be coated to a thickness of about 0.5 mil (0.012 mm) over aluminum foil layer 82 forming adhesive layer 92. The same adhesive composition may be coated to a thickness of about 0.5 mil (0.012 mm) forming adhesive layer 61 over coulometric cathode substrate end 42(b).

The auxiliary cell insulator 85 may suitably be formed of a heat sealable film of polyvinylacetate/polyvinylchloride. Alternatively, it may be composed of a butyl rubber pressure sensitive adhesive such as Butyl 065 rubber from Exxon Co. Insulator 85 is advantageously between about 1 and 2 mil (0.025 mm and 0.05 mm) thick.

Coulometer backing adhesive 32 may be selected from a wide variety of pressure sensitive adhesives. Desirably adhesive 32 is composed of a butyl rubber pressure sensitive adhesive such as Butyl 065 rubber from Exxon Co.

Figure 5:
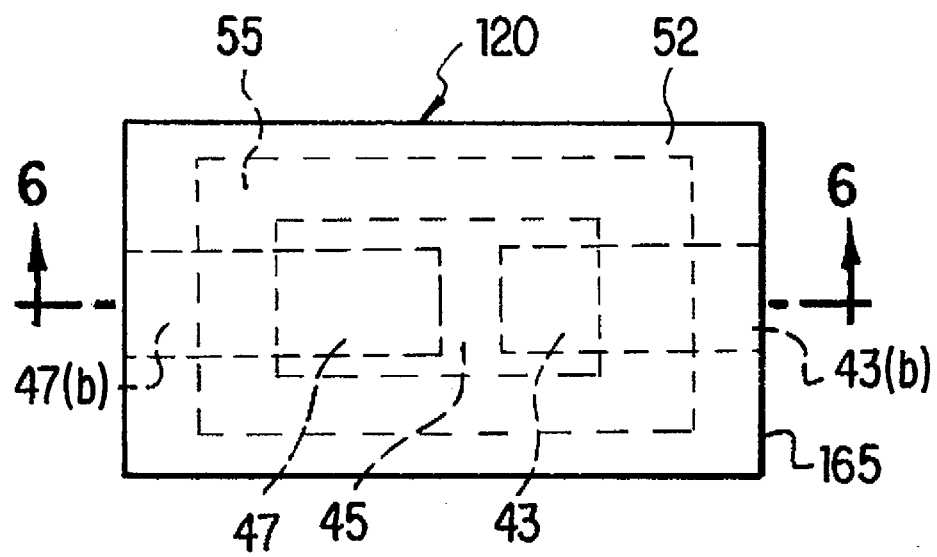
FIG. 5 is a plan view of an alternative embodiment of the coulometer cell.
Figure 6:
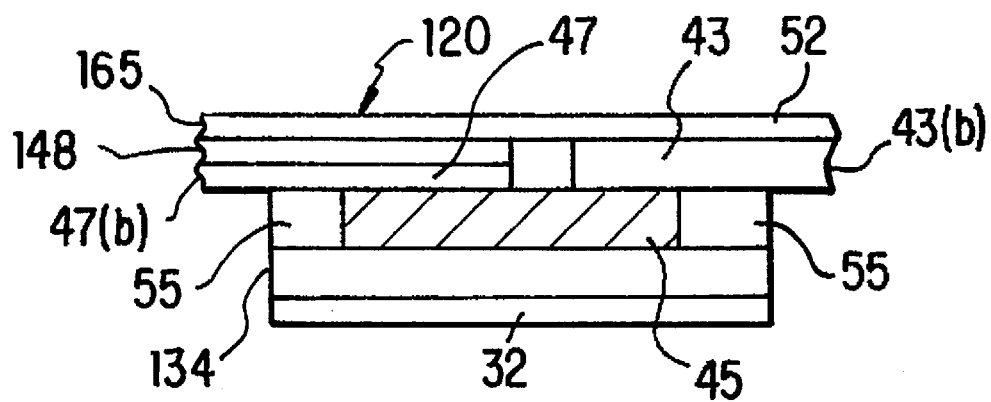
FIG. 6 is a cross sectional view of the coulometer cell taken through sight lines 6—6 of FIG. 5.

An alternative embodiment of the coulometer cell is shown as coulometric cell 120 in FIGS. 5 and 6. Coulometer cell 120 may be substituted for cell 20 in FIG. 2. Coulometric cell 120 differs from cell 20 in that it has a transparent conducting substrate 148 for anode 47. Anode 47 is deposited on the transparent conducting substrate 148 and thus transparent conducting substrate 148 lies between transparent barrier layer 52 and anode 47 (FIG. 6). Cathode 43 is deposited directly under the barrier layer 52 without need for any substrate 148 therebetween. As thus manufactured, transparent barrier 52, transparent substrate 148, anode 47, and cathode 43 together comprise a single discrete subassembly 165 when coulometer 120 is assembled. Coulometer 120 is assembled by applying an adhesive border 55 (FIG. 6) around a barrier layer 134. Adhesive border 55 defines a window area that may be filled with electrolyte 45. Coulometer 120 may then be assembled by applying subassembly 165 in contact with adhesive border 55 as shown in FIG. 6. Anode end 47(b) and cathode end 43(b) extend beyond adhesive border 55 to serve as electrical contacts. Coulometer 120 is applied to the cell with insulating layer 134 closest to the cell casing. In this embodiment, anode 47 (FIG. 5) is viewable through overlying transparent barrier 52 and transparent conducting layer 148, and therefore electrolyte 45 need not be clear as in the FIG. 2 embodiment, but rather may be colored to provide contrast as anode 47 becomes depleted. If electrolyte 45 is clear than underlying barrier layer 134 should be colored to provide the necessary contrast.

Preferred materials for transparent conducting substrate 148 include indium tin oxide and other transparent semiconductors which are readily deposited by thin film deposition techniques such as sputtering. Preferred materials for barrier film 52 include poly(ethylene naphthalate) and other chemically inert transparent films which are stable to high temperatures encountered during thin film depositions. The insulating layer 134 may be of Aclar or Kalodex material which is undercoated contact adhesive, for example adhesive 32 above described, to ensure bonding of layer 134 to the main cell 30 casing. Coulometer may be connected to auxiliary cell 25 and to the main cell 30 in manner analagous to that described with reference to FIG. 2.

Figure 3:
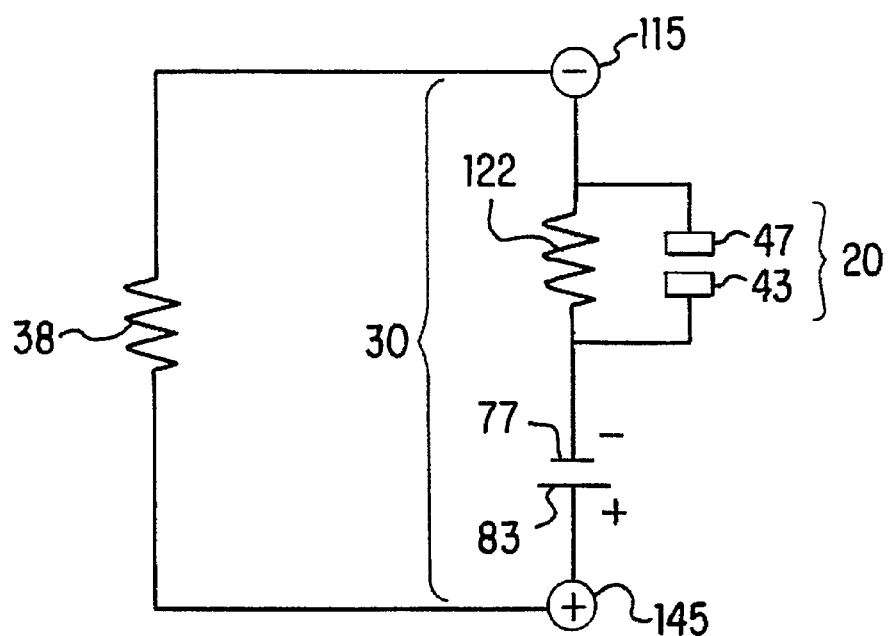
FIG. 3 is a circuit diagram showing an alternative embodiment whereby the coulometric cell is connected across a shunt resistor on the anode side of the main cell being tested.

In an alternative embodiment the auxiliary cell 25 may be eliminated and coulometer cell 20 or 120 may be connected directly to main cell 30. This can be achieved by placing a shunt resistor within the main cell being tested. In such case the shunt resistor, shown as resistor 122, may be placed on the anode side of main cell 30 consistent with the circuit diagram of FIG. 3. Alternatively, the shunt resistor, shown as resistor 112, may be placed on the cathode side of main cell 30 consistent with the circuit diagram of FIG. 4. The shunt resistor 112 or 122 may be set at appropriate values, desirably between about 1 and 10 milliohms, to ensure that the percent rate of depletion of anode 47 of the coulometer cell is about the same as the percent rate of depletion of the controlling anode or cathode of main cell 30, irrespective of the load 38 on the main cell. (The main cell electrode not in excess may be considered controlling.) Thus, as in the preceding embodiment the remaining amount of anode 47 in the coulometric cell provides a continual visual indication of the state of charge of main cell 30.

Figure 3A:
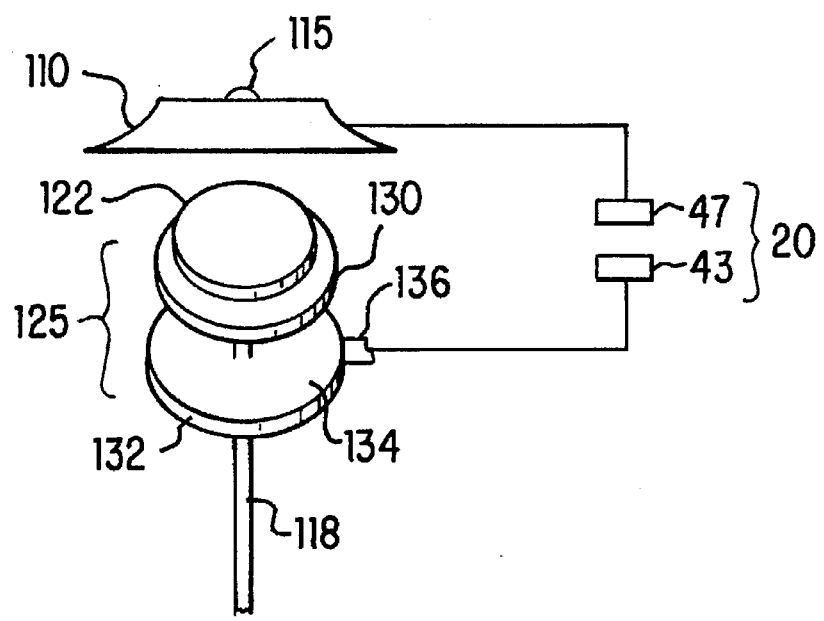
FIG. 3A is a partial perspective view showing the shunt resistor of FIG. 3 forming a portion of the anode side of a main cell being tested.

Shunt resistor 122 can be placed at the anode side of main cell 30 (FIG. 3) by adding resistor 122 in series between the main cell anode 77 and the negative terminal 115. This can be achieved by attaching a metal resistance disk 122 in series between current collector 118 and end cap 110 as shown in FIG. 3A. (Elongated metal members called a current collectors which connect the anode end cap with anode active material in the cell are commonly employed in conventional cells.) Current collector 118 may be attached to one side of disk 122 and the other side of disk 122 may be attached to end cap 110 (FIG. 3A).

In order to connect coulometric cell 20 across resistance disk 122, current collector 118 is passed through an additional disk 125 composed of a conductive surface 134 sandwiched between two insulating layers 130 and 132 so that current collector 118 makes electrical contact to conductive surface 134. Insulating layers 130 and 132 protect conductive layer 134 and prevent electrical shorting between the battery can and the end cap 110. Conductive layer 134 may be formed by depositing a conductive material such as silver onto insulating disk 132. Disk 132 may be selected from a wide range of chemically resistant plastics, preferably nylon. A conductive tab 136 may be provided and is composed of a portion of conductive layer 134 on disk 132 extending from an edge of the disk. Coulometric cell 20 may thus be connected across resistance disk 122 by electrically connecting the coulometric anode 47 to the negative endcap 110 of the main cell and by electrically connecting the coulometric cathode 43 to conductive tab 136. Resistance disk 122 may be advantageously formed of a semiconducting material, preferably with conductivity in the 10 to 50 $ohm^{-1}/cm$ range. Suitable intrinsic semiconductors may include Si, Ge, sulfides such as ZnS or $FeS_2$, or oxides such as $SnO_2$. Conductive layer 134 may be of conductive material such as silver and insulating disks 130 and 132 may be of chemically resistant insulating plastic such as nylon.

Figure 4:
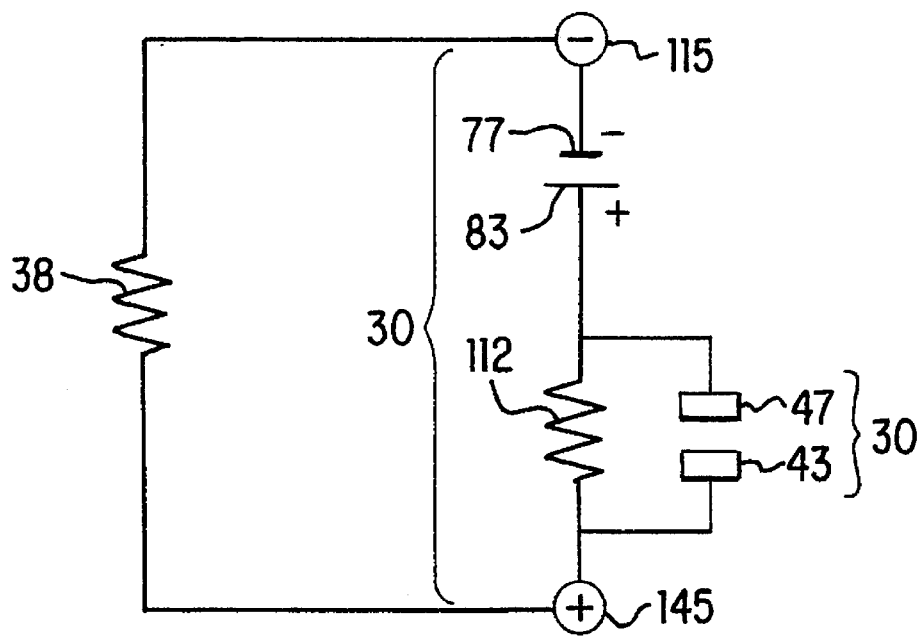
FIG. 4 is a circuit diagram showing an alternative embodiment whereby the coulometric cell is connected to a shunt resistor on the cathode side of the main cell.
Figure 4A:
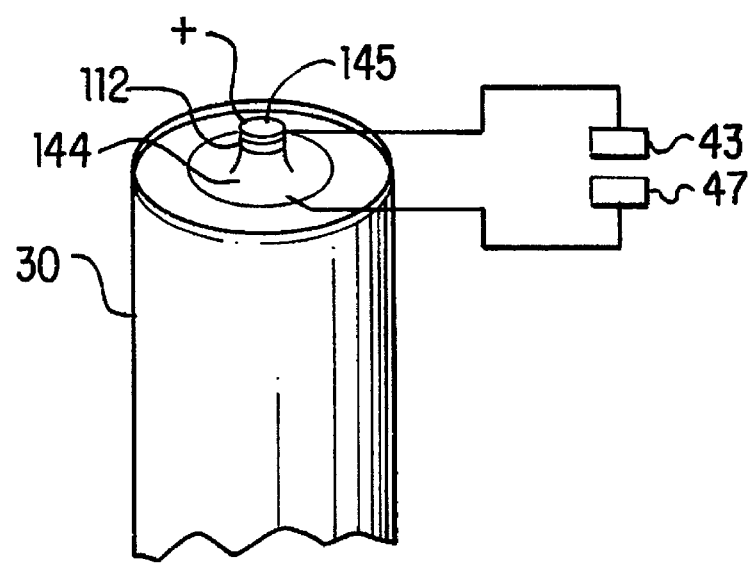
FIG. 4A is a partial exploded view of an alternative embodiment showing the shunt resistor of FIG. 4 forming a portion of the cathode side of the main cell being tested.

Alternatively, a shunt resistor, represented as resistor 112, may be placed within the main cell 30 at the cathode side thereof consistent with the circuit diagram depicted in FIG. 4. This may be carried out in a practical manner by adding the additional resistance 112 between the positive terminal 145 and the main cell cathode as shown in FIG. 4A. This can be done by increasing the depth of positive terminal 145 by adding semiconductor material such as those listed above between positive terminal 145 and the main cell casing 144. The coulometer anode 47 is then contacted to casing 144 and the coulometer cathode 43 is contacted to positive terminal 145.

In the above described embodiments (FIGS. 3A and 4A) the shunt resistor 122 or 112 desirably has a resistance less than about 10 percent of the internal resistance of the main cell being tested. Thus, if the main cell is a conventional alkaline cell having an internal resistance of about 0.1 ohm, the shunt resistor may desirably have a resistance of less than about 0.01 ohm. A higher shunt resistance is possible for acceptable operation of the coulometric cell, but such higher shunt resistance tends to interfere too much with proper operation of the main cell. Although the embodiments (FIGS. 3A and 4A) may be employed without a auxiliary cell, the use of a auxiliary cell is advantageous because it results in a more stable and reliable coulometric cell. During discharge of the main cell the voltage drop across the shunt resistor varies according to load resistance 38, and may typically be of the order of about 1 to 10 millivolts for load resistance of between about 1 and 10 ohms. Therefore to be used with such a shunt resistor, the coulometer cell should have a high electrochemical activity to be capable of operating at such small voltages. Silver electolytes such as aqueous silver perchlorate have sufficiently high electrochemical activity and are desirable.

The following is a working example of the tester described with reference to FIG. 2:

EXAMPLE 1

Working testers of the type described in the preferred embodiment (FIG. 2) are constructed and used to indicate the state of charge of AA alkaline cells discharged through various loads.

Coulometer cells as described with reference to FIG. 2 are prepared with the following components: The coulometer anode and cathode are prepared by sputter-depositing 1000 angstrom of silver onto conducting carbon coated substrates (from Creative Materials Inc.) consisting of 1 mil thick KAPTON polyimide film with 0.1 mil thick carbon/binder coating. The cathode substrates are about 0.47 in. long by 0.20 in. wide and anode substrates are about 0.86 in. long by 0.20 in wide. Cathodes are about 0.16 in. long by 0.20 in. wide and anodes are about 0.40 in. long by 0.20 in. wide, giving the anodes a capacity of about $14 \times 10^{-6}$ Amp.hr. The cathode is separated from anode by a gap of about 0.05 in. within a 2.5 mil thick butyl rubber pressure sensitive adhesive window having an interior space about 0.66 in. long by 0.30 in. wide. Anode and cathode are contacted by 2 mil thick transparent electrolyte about 0.61 in. long by about 0.25 in. wide consisting of 0.35M AgTFSI (silver trifluoromethanesulfonylimide) in solvent and prepared as previously described for the preferred embodiment. 1 mil thick ACLAR 33C transparent barrier film about 1.06 in. long by 0.60 in. wide is used to seal the coulometers. Finished coulometers are between about 6 and 7 mil (0.15 and 0.18 mm) thick and have AC resistances measured at 1 kHz of about 4 k-ohm.

Auxiliary cells of the type described with reference to FIG. 2 are prepared with the following components. The auxiliary cell cathode is prepared by coating a manganese dioxide layer containing electrolytic manganese dioxide (EMD) on a conductive substrate composed of Rexham Graphics no. 2664-01 conducting carbon-filled plastic film as previously described. The manganese dioxide coating is applied as a 0.5 mil thick wet film having dry composition which is 72% EMD and 18% graphite. The manganese dioxide layer has an area of about 0.018 $in^2$ in order to give capacity of about $14 \times 10^{-6}$ Amp-hr. The auxiliary cell anode is prepared by applying a zinc coating on Rexham Graphics no. 2664-01 conducting carbon-filled plastic substrate as described in the preceding description. The dry zinc anode has thickness of about 1 mil and about 0.070 $in^2$ area to give capacity several fold in excess of that of the cathode. The separator is prepared employing 1 mil thick Courtaulds 350 POO cellophane material containing a about $6 \times 10^{-6}$ liter of pH 4 (28% $ZnCl_2$) electrolyte. Adhesive 85 is a 2 mil thick butyl rubber pressure sensitive adhesive (Butyl rubber 065 adhesive from Exxon) used to seal the auxiliary cell. Finished auxiliary cells are about 8 mil thick and had alternating current resistance measured at 1 kHz of about 2 k-ohm. The finished testers in this example have a thickness between about 6 and 8 mils (0.15 and 0.2 mm).

Coulometer and auxiliary cells are contacted to each other in side-by-side arrangement as in FIG. 2 and to fresh AA alkaline cells (FIG. 2A) using ARCLAD 0.5 mil thick conductive adhesive (61 and 92) as previously described. The AA cells are discharged from 1.5 to 0.8 volts through load resistors of either 1 ohm, 4 ohm, 36 ohm, or 75 ohm, either continuously or intermittently. During discharge in each case the voltage across the coulometer cell is small. For example, for a 4 ohm load, the voltage across the coulometer cell is between about 40 and 100 millivolts and the current through the coulometer cell is about $2 \times 10^{-6}$ amps. In all cases the coulometer anode clears in a gauge-like fashion to visually reveal the underlying black conducting substrate (48), with the clearing beginning from the end (47(a)) closest to the cathode and proceeding towards the opposite end of the cathode. The amount of clearing correlates linearly proportional with the extent of discharge of the AA cell. Thus the tester serves as an effective state of charge indicator for the main cell.

The coulometric cell embodiments herein described can be employed advantageously to test the condition of conventional $Zn/MnO_2$ alkaline cells which may operate typically with load resistance between about 1 and 1000 ohms. The application of the invention, however is not intended to be limited to alkaline cells but rather may be used effectively to test the condition of any dry cell.

Although the present invention has been described with reference to specific embodiments and specific materials of construction, it will be appreciated that other embodiments and materials are possible without departing from the concept of the invention. Therefore, the invention is not intended to be limited to specific embodiments described herein, but rather the scope of the invention is defined by the claims and equivalents thereof.

What is claimed is:

1. A condition indicator for an electrochemical power source, said condition indicator comprising an electrolytic cell having essentially no electromotive force (e.m.f.) of its own, said electrolytic cell comprising an anode, a cathode, and an electrolyte, said electrolyte electrically contacting at least a portion of both said anode and cathode, and said condition indicator further comprising an auxiliary cell electrically connected in series to the electrolytic cell, wherein the auxiliary cell is an electrochemical power generating cell, and wherein said power source is an electrochemical cell other than the auxiliary cell, the electrochemical power source comprising a positive and a negative terminal whereinsaid electrochemical power source is electrically connected to the auxiliary cell with one of (i) and (ii) being in effect, said (i) being the positive terminal of said electrochemical power source electrically connected to the cathode of the auxiliary cell and said (ii) being the negative terminal of said electrochemical power source electrically connected to the anode of the auxiliary cell.

2. The condition indicator of claim 1 wherein at least a portion of one of said anode and cathode is visible, and wherein during electrolysis in the electrolytic cell reaction begins at a first region of said visible electrode and continues therefrom towards remote regions thereof.

3. The combination of a battery and a battery condition indicator, wherein said battery comprises a casing, a negative terminal, and a positive terminal and said condition indicator comprises an electrolytic cell having essentially no electromotive force (e.m.f.) of its own, said electrolytic cell comprising an anode, a cathode, and an electrolyte, said electrolyte electrically contacting at least a portion of both said anode and cathode, said condition indicator being permanently electrically connected to the battery, wherein said condition indicator further comprises an auxiliary cell electrically connected in series to the electrolytic cell, wherein the auxiliary cell is an electrochemical cell other than the battery, said auxiliary cell comprising an anode, a cathode, and an electrolyte contacting at least a portion of said auxiliary cell anode and cathode, wherein the battery is electrically connected to the auxiliary cell with one of (i) add (ii) being in effect, said (i) being the positive terminal of the battery electrically connected to the cathode of the auxiliary cell and said (ii) being the negative terminal of said battery electrically connected to the anode of the auxiliary cell, wherein at least one of said anode and cathode of the electrolytic cell being visible and wherein during discharge of said battery reaction begins at a first region of said visible electrode and continues therefrom towards remote regions thereof.

4. The combination of claim 3 wherein the auxiliary cell cathode is electrically connected to the positive terminal of the battery and the auxiliary cell anode is electrically connected to the cathode of the electrolytic cell and the anode of the electrolytic cell is electrically connected to the negative terminal of the battery.

5. The combination of claim 3 wherein the auxiliary cell anode is electrically connected to the negative terminal of the battery and the auxiliary cell cathode is electrically connected to the anode of the electrolytic cell and the cathode of the electrolytic cell is electrically connected to the positive terminal of the battery.

6. The combination of claim 3 wherein the condition indicator is integrated into a label for said battery.

7. The combination of claim 3 wherein said battery comprises an elongated current collector in electrical contact with said negative terminal, wherein said battery further comprises a resistive element located along the length of said current collector, and wherein the electrolytic cell is electrically connected across said resistive element so that said resistive element functions as a shunt resistor for said electrolytic cell.

8. The combination of claim 3 wherein said battery further comprises a resistive element located between said positive terminal and said casing , and wherein the electrolytic cell is electrically connected across said resistive element so that said resistive element functions as a shunt resistor for said electrolytic cell.

9. The combination of claim 3 wherein the electrolytic cell anode and cathode comprise the same electrochemically active material.

10. The combination of claim 3 wherein the anode and cathode of the electrolytic cell are laterally spaced apart so that no portion of the electrolytic cell anode overlaps any portion of the electrolytic cell cathode.

11. The combination of claim 3 wherein the anode and cathode of the electrolytic cell both comprise silver.

12. The combination of claim 3 wherein the cell condition indicator has a thickness of less than about 100 mils (2.5 mm).

13. The combination of claim 3 wherein the condition indicator has a thickness between about 2 and 15 mils (0.05 and 0.4 mm).

* * * * *